United States Patent
Kim et al.

(10) Patent No.: US 9,414,801 B2
(45) Date of Patent: Aug. 16, 2016

(54) X-RAY IMAGING APPARATUS AND CONTROL METHOD THEREFOR

(71) Applicant: SAMSUNG ELECTRONICS CO., LTD., Suwon-si (KR)

(72) Inventors: Jong Pil Kim, Yongin-si (KR); So Dam Baek, Jeonju-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 160 days.

(21) Appl. No.: 14/193,791

(22) Filed: Feb. 28, 2014

(65) Prior Publication Data
US 2015/0245806 A1  Sep. 3, 2015

(51) Int. Cl.
*A61B 6/06* (2006.01)
*G21K 1/04* (2006.01)
(Continued)

(52) U.S. Cl.
CPC .............. *A61B 6/544* (2013.01); *A61B 5/0531* (2013.01); *A61B 5/103* (2013.01); *A61B 5/107* (2013.01);
(Continued)

(58) Field of Classification Search
CPC ........ A61B 6/0414; A61B 6/06; A61B 6/502; A61B 6/5258; A61B 6/542; A61B 6/4291; A61B 6/4233; A61B 6/025; A61B 6/04; A61B 6/482; A61B 6/585; A61B 6/107; A61B 6/488; A61B 6/0421; A61B 6/4417; A61B 6/463; A61B 6/464; A61B 6/465; A61B 6/583; A61B 6/4035; A61B 6/037; A61B 6/4494; A61B 6/08; A61B 6/4208; A61B 6/4266; A61B 6/44; A61B 6/4405; A61B 6/461; A61B 6/547; A61B 6/587; A61B 5/05; A61B 5/053; A61B 5/0531; A61B 5/103; A61B 5/107; A61B 5/1072; A61B 5/1075; A61B 5/1077; A61B 5/68; A61B 5/6887; A61B 5/6891; A61B 5/6892; A61B 5/70; A61B 5/708; A61B 6/00; A61B 6/0407; A61B 6/0492; A61B 6/40; A61B 6/405; A61B 6/42; A61B 6/4283; A61B 6/4476; A61B 6/46; A61B 6/467; A61B 6/469; A61B 6/50; A61B 6/5252; A61B 6/54; A61B 6/544; A61B 6/545; A61B 6/58; A61B 6/582; G01T 1/00; G03B 42/02; G21K 1/00; G21K 1/02; G21K 1/04; G21K 1/046; H05G 1/00; H05G 1/02; H05G 1/08; H05G 1/60; H01J 35/00; H01J 35/02; H01J 35/025; H01J 35/16; H01L 23/58; H01L 23/64; H01L 23/642; H01L 23/647; H01L 27/14678; G01R 27/00; G01R 27/02; G01R 27/08; G01R 27/14; G01R 27/26; G01R 27/2605; G01B 7/00; G01B 7/003; G01B 7/02; G01B 7/12; G01B 7/32; G01B 21/28; G06G 7/00; G06G 7/04; G06G 7/66; B25J 9/1694
USPC ...................................... 378/37, 62
See application file for complete search history.

(56) References Cited

U.S. PATENT DOCUMENTS 5,627,869 A * 5/1997 Andrew ................. A61B 6/502
378/150
7,251,309 B2  7/2007 Galkin
2008/0112534 A1  5/2008 Defreitas et al.

FOREIGN PATENT DOCUMENTS

EP  2 103 257 A1  9/2009
FR  2 881 337 A1  8/2006
(Continued)

OTHER PUBLICATIONS

Communication dated May 26, 2014, issued by the European Patent Office in counterpart European Application No. 14150877.0.
(Continued)

*Primary Examiner* — Anastasia Midkiff
(74) *Attorney, Agent, or Firm* — Sughrue Mion, PLLC

(57) ABSTRACT

Disclosed herein are an X-ray imaging apparatus and a control method therefor in which a region of a compressed breast is measured by a touch sensor and a collimator is controlled such that an X-ray emission region corresponds to the measured region of a compressed breast, whereby workflow for performing X-ray imaging may be reduced and subject pain due to breast compression may be alleviated. The X-ray imaging apparatus includes an X-ray source to generate X-rays and irradiate an object with the generated X-rays, a collimator to adjust an emission region of the X-rays generated from the X-ray source, an X-ray detector to detect X-rays having passed through the object to acquire X-ray data, a touch sensor disposed above the X-ray detector, a compression paddle to compress the object placed on the touch sensor, and a collimator control unit to calculate location and size of the compressed object based on an output value of the touch sensor and control the collimator based on calculation results.

20 Claims, 16 Drawing Sheets

(51) Int. Cl.
- *H01J 35/02* (2006.01)
- *G01B 7/32* (2006.01)
- *G06G 7/04* (2006.01)
- *H01L 23/64* (2006.01)
- *A61B 6/04* (2006.01)
- *A61B 5/00* (2006.01)
- *A61B 6/00* (2006.01)
- *A61B 5/103* (2006.01)
- *A61B 5/107* (2006.01)
- *B25J 9/16* (2006.01)
- *A61B 5/053* (2006.01)
- *G01B 7/00* (2006.01)

(52) U.S. Cl.
CPC ............... *A61B 5/708* (2013.01); *A61B 6/0414* (2013.01); *A61B 6/469* (2013.01); *A61B 6/5252* (2013.01); *A61B 6/542* (2013.01); *A61B 6/545* (2013.01); *B25J 9/1694* (2013.01); *G01B 7/32* (2013.01); *A61B 5/053* (2013.01); *A61B 5/6887* (2013.01); *A61B 6/06* (2013.01); *A61B 6/4035* (2013.01); *A61B 6/502* (2013.01); *G01B 7/003* (2013.01); *G06G 7/04* (2013.01); *G21K 1/046* (2013.01); *H01J 35/025* (2013.01); *H01L 23/642* (2013.01); *H01L 23/647* (2013.01)

(56) References Cited

FOREIGN PATENT DOCUMENTS

| JP | 08-238237 A | 9/1996 |
| JP | 2008006186 A | 1/2008 |
| JP | 2012228433 A | 11/2012 |

OTHER PUBLICATIONS

Communication dated Jan. 21, 2014, issued by the Korean Intellectual Property Office in counterpart Korean Application No. 10-2013-0004144.

\* cited by examiner

X-RAY IMAGING APPARATUS AND CONTROL METHOD THEREFOR

BACKGROUND

1. Field

Embodiments of the present invention relate to an X-ray imaging apparatus to generate an X-ray image by passing X-rays through an object and a control method therefor.

2. Description of the Related Art

X-ray imaging apparatuses are devices to irradiate an object with X-rays and acquire an image of the interior of the object using X-rays having passed through the object. The penetration of X-rays varies according to properties of materials constituting the object, and thus, an internal structure of the object may be imaged by detecting the intensity of X-rays having passed through the object.

Among these X-ray imaging apparatus, a mammography apparatus examines breasts as an object. Breasts contain mammary gland tissues and adipose tissues, and thus, X-ray imaging needs to be performed in a state in which a breast placed between an X-ray source and an X-ray detector is compressed using a compression paddle in order to acquire an X-ray image that clearly shows an internal structure of the breast.

A radiologist manually adjusts an emission region of X-rays in a state in which a breast of a subject is compressed, and thus, workflow needed for X-ray imaging is increased and subject pain due to breast compression are also increased.

SUMMARY

Therefore, it is an aspect of the present invention to provide an X-ray imaging apparatus and a control method therefor in which a region of a compressed breast is measured by a touch sensor and a collimator is controlled such that an X-ray emission region corresponds to the measured region of a compressed breast, whereby workflow for performing X-ray imaging may be reduced and subject pain due to breast compression may be alleviated.

Additional aspects of the invention will be set forth in part in the description which follows and, in part, will be obvious from the description, or may be learned by practice of the invention.

In accordance with one aspect of the present invention, an X-ray imaging apparatus includes an X-ray source to generate X-rays and irradiate an object with the generated X-rays, a collimator to adjust an emission region of the X-rays generated from the X-ray source, an X-ray detector to detect X-rays having passed through the object to acquire X-ray data, a touch sensor disposed above the X-ray detector, a compression paddle to compress the object placed on the touch sensor, and a collimator control unit to calculate location and size of the compressed object based on an output value of the touch sensor and control the collimator based on calculation results.

The collimator control unit may determine an object region according to the location and size of the compressed object and set an X-ray emission region corresponding to the object region.

The collimator control unit may control the collimator such that the X-rays generated from the X-ray source are emitted to the set X-ray emission region.

The X-ray imaging apparatus may further comprise an image controller to remove error due to the touch sensor from the X-ray data.

The collimator may include at least one blade movable in an X-axis direction and at least one driving unit to drive the at least one blade.

The at least one driving unit may move the at least one blade in an X-axis direction according to a control signal transmitted from the collimator control unit.

The collimator control unit may calculate a displacement of the at least one blade, for correspondence between the X-ray emission region and the object region.

The collimator control unit may transmit a control signal to the at least one driving unit so that the at least one blade is moved by the calculated displacement.

The collimator may include a plurality of blades, the blades being each independently moved in an X-axis or Y-axis direction.

The touch sensor may be at least one selected from the group consisting of a capacitive touch sensor and a resistive touch sensor.

In accordance with another aspect of the present invention, a method of controlling an X-ray imaging apparatus including an X-ray source to generate X-rays and irradiate an object with the generated X-rays, a collimator to adjust an emission region of the X-rays generated from the X-ray source, and an X-ray detector to detect X-rays having passed through the object includes compressing the object placed on a touch sensor installed above the X-ray detector, calculating location and size of the compressed object based on an output value of the touch sensor, and controlling the collimator based on calculation results.

The controlling may include determining an object region according to the location and size of the compressed object and setting an X-ray emission region corresponding to the object region.

The controlling may further include controlling the collimator such that the X-rays generated from the X-ray source are emitted to the set X-ray emission region.

The method may further include generating X-rays from the X-ray source, emitting the X-rays via the controlled collimator, detecting the emitted X-rays through the X-ray detector to acquire X-ray data of the object, and removing error due to the touch sensor from the X-ray data of the object.

The collimator may include at least one blade movable in an X-axis direction.

The controlling may include moving the at least one blade in an X-axis direction.

The controlling may include comprises calculating a displacement of the at least one blade, for correspondence between the X-ray emission region and the object region.

The controlling may include moving the at least one blade by the calculated displacement.

The collimator may include a plurality of blades, the controlling comprising each independently moving the blades in an X-axis direction.

The touch sensor may be at least one selected from the group consisting of a capacitive touch sensor and a resistive touch sensor.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
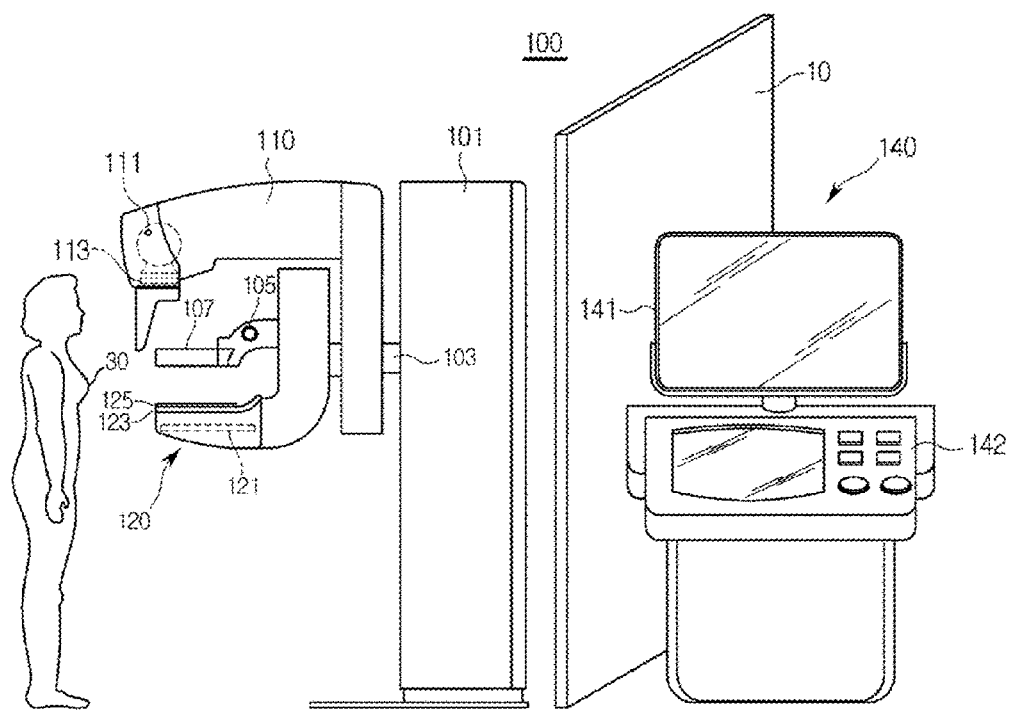
FIG. 1 is an overall exterior view of an X-ray imaging apparatus according to an embodiment of the present invention.

Reference will now be made in detail to the embodiments of the present invention, examples of which are illustrated in the accompanying drawings, wherein like reference numerals refer to like elements throughout.

Hereinafter, embodiments of the present invention will be described in detail with reference to the accompanying drawings.

Figure 2:
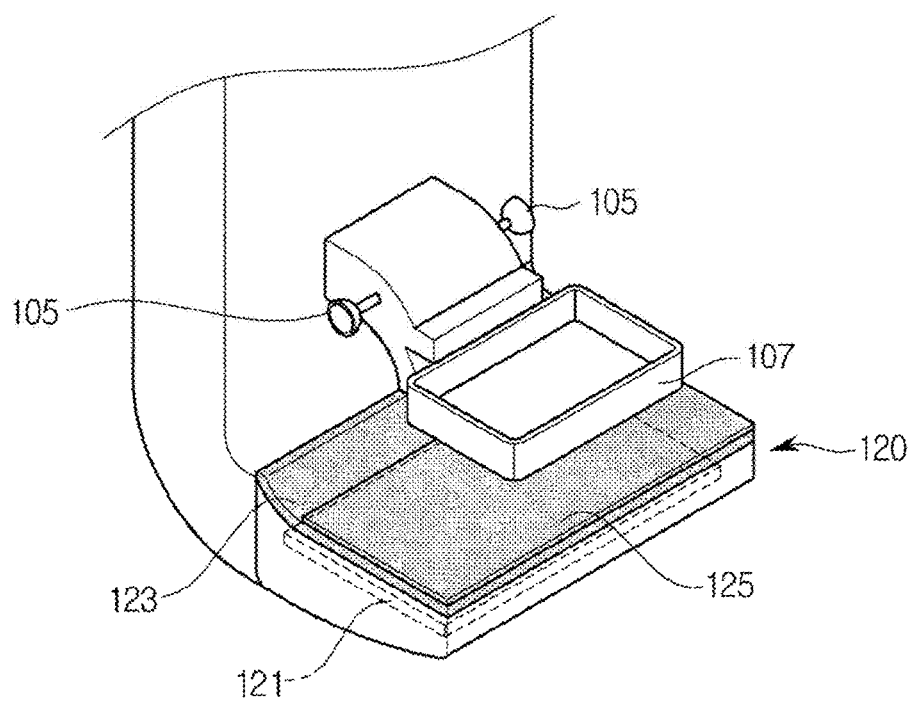
FIG. 2 is an enlarged view of an X-ray detection unit equipped with a touch sensor.

FIG. 1 is an overall exterior view of an X-ray imaging apparatus 100 according to an embodiment of the present invention. FIG. 2 is an enlarged view of an X-ray detection unit equipped with a touch sensor 125.

The X-ray imaging apparatus 100 according to an embodiment of the present invention may perform imaging of breasts. An X-ray imaging apparatus for mammography is configured to emit X-rays in a state in which a breast is compressed, in terms of characteristics of breasts with mammary gland tissues and adipose tissues. Hereinafter, the configuration of the X-ray imaging apparatus 100 will be described in detail with reference to FIGS. 1 and 2.

Referring to FIG. 1, the X-ray imaging apparatus 100 includes an X-ray generator 110 to generate X-rays and irradiate an object 30 with the generated X-rays, an X-ray detection unit 120 to detect X-ray having passed through the object 30, and a compression paddle 107 to compress the object 30 disposed on the X-ray detection unit 120. The X-ray generator 110 and the X-ray detection unit 120 are connected to a housing 101 via a connection arm 103, and the housing 101 supports the X-ray generator 110 and the X-ray detection unit 120.

The X-ray generator 110 includes an X-ray source 111 to generate X-rays and a collimator 113 to adjust an emission region of X-rays emitted from the X-ray source 111. A detailed description of the X-ray source 111 and the collimator 113 will be provided below.

When the object 30 is a breast, it is necessary to reduce the thickness of the breast by compressing the breast in a direction perpendicular to the ground, to acquire a clearer, more accurate image. Thus, the breast 30 is positioned between the compression paddle 107 and the X-ray detection unit 120, and X-rays are emitted in a state in which the object 30 is compressed by the compression paddle 107. The compression paddle 107 may move upward or downward by operating a compression paddle adjustment lever 105.

The X-ray detection unit 120 includes an X-ray detector 121 to detect X-rays having passed through the object 30, convert the detected X-rays into an electrical signal, and acquire X-ray data from the electrical signal and is provided with a sheet 123 that is disposed on a housing accommodating the X-ray detector 121 and serves to mount the object 30, i.e., a breast. The sheet 123 may be made of a material and a color that minimally affects passage of X-rays. For example, the sheet 123 may be a carbon sheet.

An X-ray detector may be classified according to composition of materials, a method of converting the detected X-rays into an electrical signal, and a method of acquiring X-ray data.

First, the X-ray detector is classified into a single element type and a hybrid element type according to composition of materials.

When the X-ray detector is of a single element type, a part to detect X-rays and generate an electrical signal using the detected X-rays and a part to read and process the electrical signal are made of a single element semiconductor or manufactured using a single process. For example, a single element type X-ray detector may be a light receiving element such as a charge coupled device (CCD) or a complementary metal oxide semiconductor (CMOS).

When the X-ray detector is of a hybrid element type, a part to detect X-rays and generate an electrical signal using the detected X-rays and a part to read and process the electrical signal are made of different materials or manufactured using different processes. For example, in a case in which X-rays are detected using a light receiving element such as a photodiode or a CCD, or a light receiving element made of CdZnTe and an electrical signal is read and processed using a CMOS read out integrated circuit (ROIC), the X-ray detector may include a strip detector to detect X-rays and a CMOS ROIC to read and process an electrical signal, or an a-Si or a-Se flat panel system may be used.

In addition, the X-ray detector is classified into a direct conversion type and an indirect conversion type according to a method of converting X-rays into an electrical signal.

In the direct conversion type, when X-rays are emitted, electron-hole pairs are temporarily generated in a light receiving element, and electrons and holes migrate to positive and negative electrodes, respectively, by an electric field applied to opposite ends of the light receiving element. In this regard, the X-ray detector converts such movement into an electrical signal. A material used in the light receiving element of the direct conversion-type X-ray detector may be a-Se, CdZnTe, $HgI_2$, $PbI_2$, or the like.

In the indirect conversion type, a scintillator is provided between a light receiving element and an X-ray generator and, when X-rays emitted from the X-ray generator react with the scintillator to release photons having a visible light wavelength, the light receiving element senses the released photons and converts the photons into an electrical signal. The light receiving element may be made of a-Si or the like, and the scintillator may be a thin film type GADOX scintillator, a micro-column type or needle structured type CSI(T1), or the like.

In addition, the X-ray detector is classified into a charge integration mode and a photon counting mode according to a method of acquiring X-ray data. The charge integration mode is a method whereby charges are stored for a certain period of time and then a signal is obtained therefrom, and the photon counting mode is a method whereby whenever a signal is generated by X-ray single photons, photons having energy that is equal to or greater than threshold energy are counted.

The X-ray detector 121 used in an embodiment of the present invention may be any of the above described types according to composition of materials, a method of conversion into an electrical signal, and an X-ray data acquisition method.

X-ray data acquired by the X-ray detector 121 are transmitted to a host device 140. The host device 140 includes a display 141 to display an X-ray image and an input unit 142 through which commands for operation of the X-ray imaging apparatus 100 are input.

The X-ray detection unit 120 further includes the touch sensor 125 to sense contact with the object 30. Referring to FIG. 2, the touch sensor 125 is disposed above the X-ray detector 121, more particularly, on the sheet 123. Thus, the breast 30, which is an object for X-ray imaging, is placed on the touch sensor 125, and a radiologist adjusts the compression paddle adjustment lever 105 to allow the compression paddle 107 to compress the breast 30 to a certain thickness.

Meanwhile, to prevent unnecessary exposure to radiation, a shielding plate 10 may be installed to separate an area for X-ray imaging of a patient from an area for a radiologist to manipulate the host device 140. The shielding plate 10 may be made of a material that absorbs X-rays, such as lead. If a radiologist visually inspects an area at which the compressed breast 30 is placed, moves to the host device 140 positioned opposite to the area for X-ray imaging, adjusts the collimator 113, and then manipulates the X-ray imaging apparatus 100 to emit X-rays to the breast 30, it takes a long time for a patient to wait in a state in which the breast 30 is compressed.

In the X-ray imaging apparatus 100 according to an embodiment of the present invention, however, the touch sensor 125 senses an area at which the breast 30 is placed and the collimator 113 is automatically controlled according to sensing results of the touch sensor 125. Accordingly, patient wait time may be reduced and unnecessary emission of X-rays may be minimized.

Figure 3:
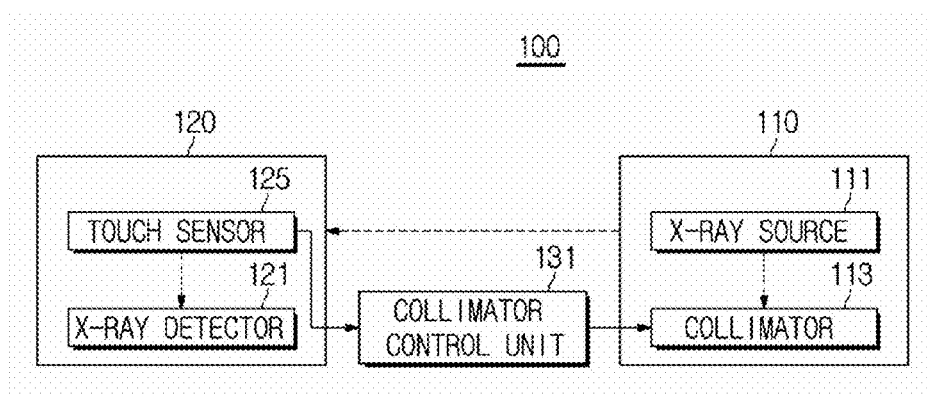
FIG. 3 is a control block diagram of the X-ray imaging apparatus according to an embodiment of the present invention.

FIG. 3 is a control block diagram of the X-ray imaging apparatus 100. In FIG. 3, solid lines denote flow of data, and dotted lines denote flow of X-rays. Hereinafter, particular operations of the X-ray imaging apparatus 100 will be described with reference to FIG. 3.

As described above, when the compression paddle 107 compresses the breast 30, the touch sensor 125 senses a region of the touch sensor 125 contacting the breast 30.

The touch sensor 125 may be a capacitive touch sensor or a resistive touch sensor. The capacitive touch sensor senses static electricity generated in a human body. When the touch sensor 125 is of a capacitive type, transparent electrodes formed of ITO are respectively coated on opposite surfaces of a base, and voltage is applied to four corners of the base so that current flows in the surface of the touch sensor 125. In this regard, when the breast 30 contacts the touch sensor 125, capacitance of the region of the touch sensor 125 contacting the breast 30 is changed. Therefore, a region in which the breast 30 is placed on the touch sensor 125 (hereinafter referred to as an "object region") may be determined from an output value of the touch sensor 125.

The resistive touch sensor senses pressure applied to the touch sensor. When the touch sensor 125 is of a resistive type, transparent electrodes formed of ITO are respectively coated on two substrates, the two substrates are spaced apart from each other by a plurality of spacers such that the coated surfaces of the respective substrates face each other. In this regard, when the breast 30 contacts the touch sensor 125, changes in current and resistance occur in a region of the touch sensor 125 contacting the breast 30 because the two substrates contact each other. Therefore, an object region may be determined from an output value of the touch sensor 125.

The capacitive and resistive touch sensors are provided for illustrative purposes only, and a structure or sensing method of the touch sensor 125 is not limited to the above examples. That is, any touch sensor capable of sensing contact with the object 30 may be used as the touch sensor 125.

The output value of the touch sensor 125 is transmitted to a collimator control unit 131, and the collimator control unit 131 that receives the output value of the touch sensor 125 may calculate location and size of the breast 30 by analyzing the transmitted output value. Then, where the breast 30 is placed on the touch sensor 125, i.e., the object region, is determined according to the location and size of the breast 30.

As illustrated in FIG. 1, the collimator 113 is disposed in front of the X-ray source 111 and thus may adjust an emission region of X-rays emitted from the X-ray source 111. Thus, the collimator control unit 131 controls the collimator 113 in order that the emission region of X-rays emitted from the X-ray source 111 corresponds to the object region. In particular, the collimator control unit 131 sets an X-ray emission region corresponding to the object region and transmits, to the collimator 113, a control signal for directing the X-rays emitted from the X-ray source 111 to the set X-ray emission region. According to an embodiment of the present invention, the X-ray emission region is a region of the touch sensor 125 in which X-rays finally reach.

When the collimator 113 is controlled, X-rays are generated from the X-ray source 111 and emitted via the collimator 113, and the emitted X-rays pass through the object 30 and the touch sensor 125 and then reach the X-ray detector 121. The X-ray detector 121 converts the X-rays into an electrical signal and acquires X-ray data for the object 30, and the acquired X-ray data are used to generate an X-ray image of the object 30. The generated X-ray image is displayed on the display 141 of the host device 140.

Hereinafter, operation of the collimator 113 will be described in detail with reference to FIGS. 4 and 5A to 5C.

Figure 4:
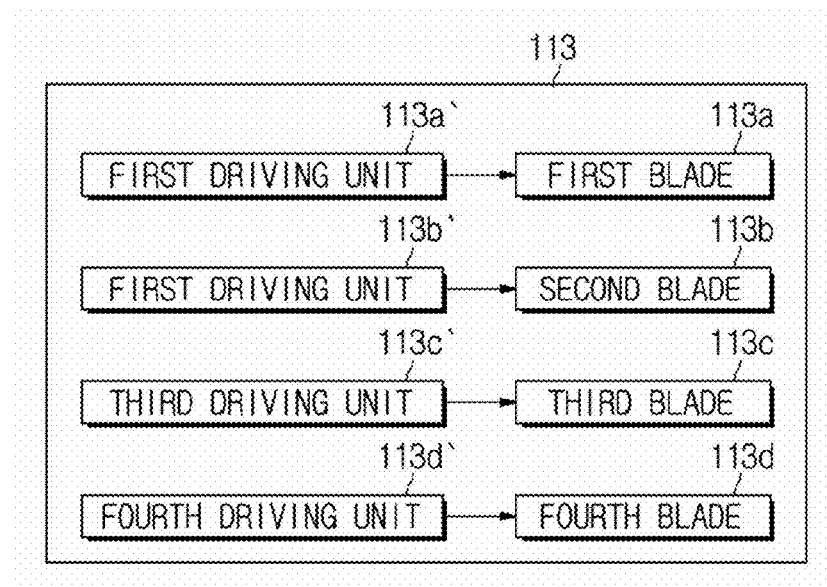
FIG. 4 is a control block diagram illustrating the configuration of a collimator.
Figure 5A:
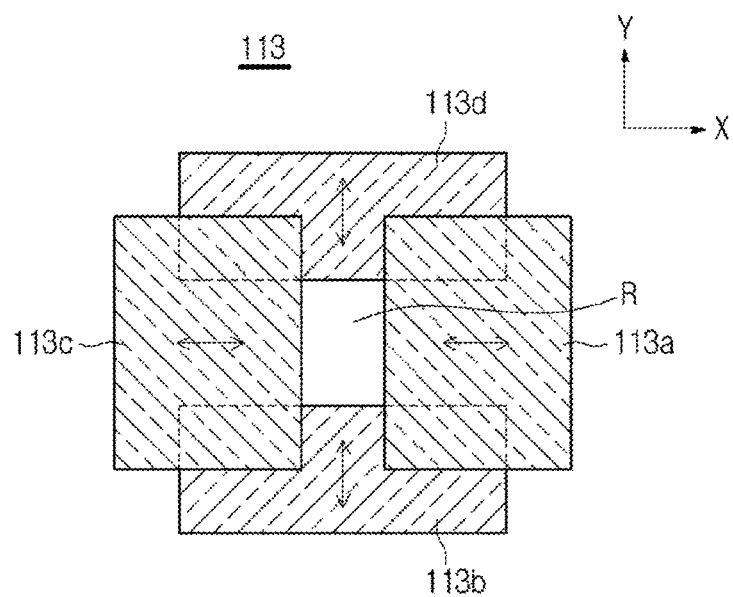
FIGS. 5A to 5C are top plan views of the collimator.
Figure 5B:
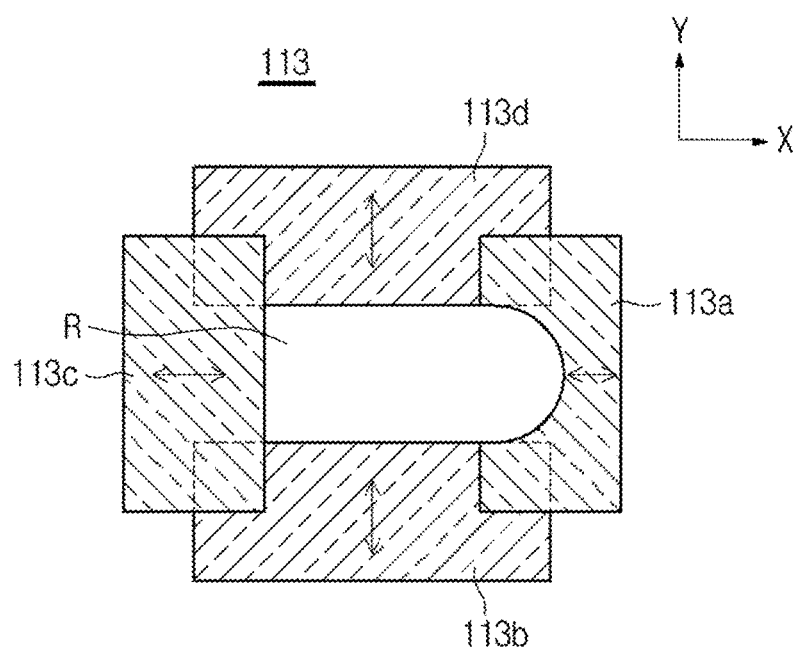
Figure 5C:
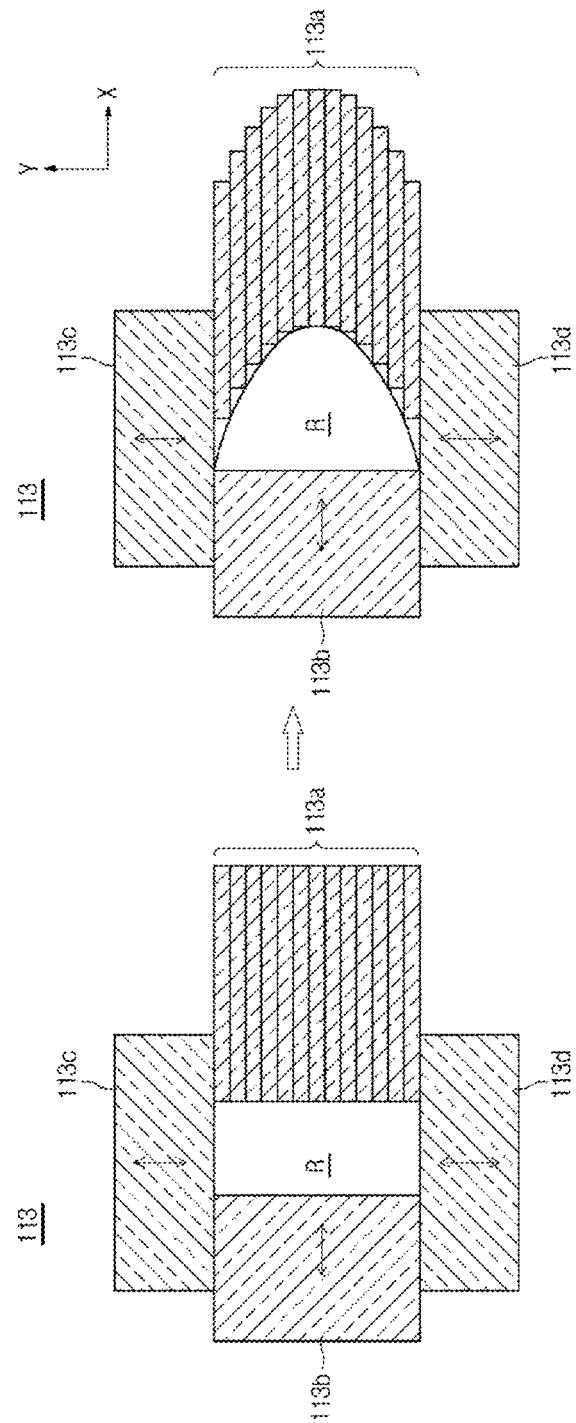

FIG. 4 is a control block diagram illustrating the configuration of the collimator 113. FIGS. 5A to 5C are top plan views of the collimator 113.

The collimator 113 includes at least one movable blade, and the blade is made of a material having a high bandgap and thus may absorb X-rays. The X-ray emission region may be adjusted while the blade moves, and the collimator 113 further includes a driving unit to provide driving force to the blade.

The collimator control unit 131 calculates a displacement of each blade in order that X-rays are emitted to the set X-ray emission region and transmits, to each driving unit, a control signal for movement of the blade by the calculated displacement.

According to an embodiment, as illustrated in FIG. 4, the collimator 113 may include four blades, i.e., first, second, third and fourth blades 113a, 113b, 113c and 113d, and four driving units, i.e., first, second, third and fourth driving units 113a', 113b', 113c' and 113d' that provide driving force to the respective blades. The blades may be each independently moved by the respective driving units corresponding thereto. Each driving unit may be made of a motor, and a linear motor may be used as the driving unit when the blade is linearly moved.

The collimator 113 illustrated in FIG. 5A has the first, second, third and fourth blades 113a, 113b, 113c and 113d each having a tetragonal shape. The first and second blades 113a and 113b are each independently movable in opposite directions of an X-axis, and the third and fourth blades 113c and 113d are each independently movable in opposite directions of a Y-axis. X-rays are emitted via an empty space R formed by the four blades and, according to an embodiment of the present invention, the empty space R is denoted as an X-ray penetration region.

An X-ray emission region means a region of the touch sensor 125 upon which X-rays are emitted, and thus, the X-ray penetration region R may or may not coincide with the X-ray emission region. In particular, when X-rays generated from the X-ray source 111 are emitted in a straight line, the X-ray penetration region R and the X-ray emission region may coincide with each other. On the other hand, when X-rays are radiated in the form of conical beams, the X-ray penetration region R and the X-ray emission region do not coincide with each other. Although the X-ray penetration region R does not coincide with the X-ray emission region, the X-ray emission region may be adjusted by adjusting the X-ray penetration region R based on a relationship between the two regions.

The structure of the collimator 113 is not limited to the embodiment illustrated in FIG. 5A and, if desired, the collimator 113 may have various shapes.

For example, as illustrated in FIG. 5B, an oval groove may be formed at one side of the first blade 113a so that the X-ray emission region most nearly approximates to the object region, i.e., a region of the breast. By such configuration, unnecessary emission of X-rays to a region outside the breast may be minimized.

In addition, as illustrated in FIG. 5C, the first blade 113a may be provided in the form of multi-leaf so that the X-ray emission region can be more precisely adjusted.

Although FIGS. 5A to 5C illustrate that the collimator 113 includes the four blades, this is provided for illustrative purposes only. That is, the shape and number of the blades of the collimator 113 are not particularly limited and, if desired, the blades may be configured in a variety of numbers.

When control of the collimator 130 is completed, X-rays are generated from the X-ray source 111, and the generated X-rays pass through the X-ray penetration region R, which are then emitted to the X-ray emission region set by the collimator control unit 131.

Figure 6:
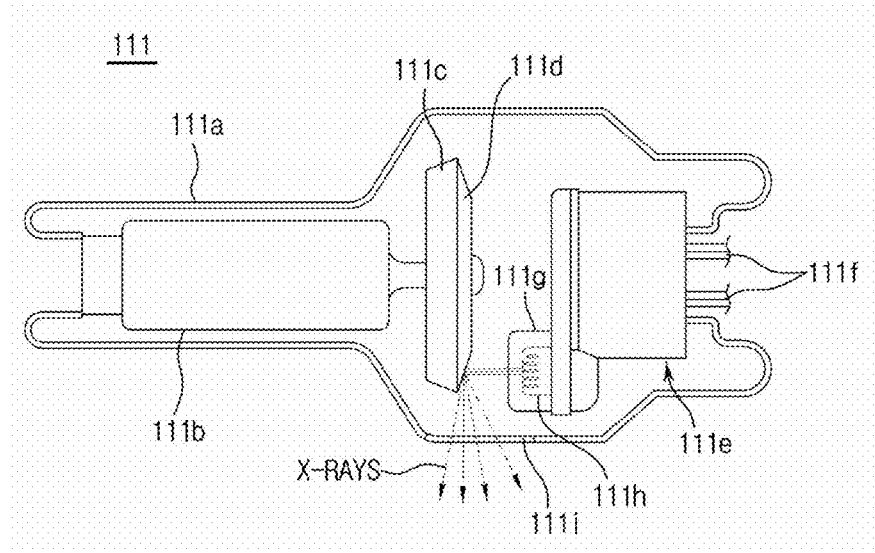
FIG. 6 is a view illustrating an inner structure of an X-ray source to generate X-rays.
Figure 7:
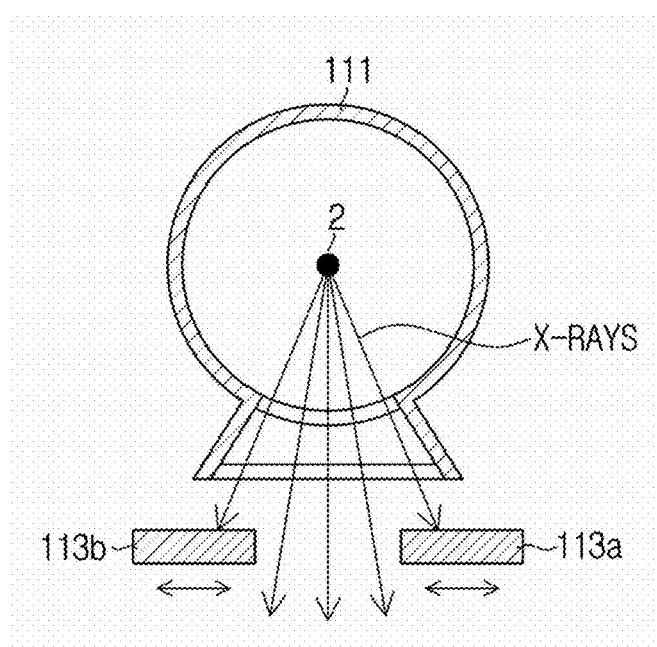
FIG. 7 is a side sectional view of the X-ray source and the collimator.

FIG. 6 is a view illustrating an inner structure of the X-ray source 111 to generate X-rays. FIG. 7 is a side sectional view of the X-ray source 111 and the collimator 113.

The X-ray source 111 may be embodied as a two-electrode vacuum tube (111a) made of positive and negative electrodes. An interior of the X-ray tube (111a) is evacuated to a high vacuum state of approximately 10 mmHg and a filament 111e of the negative electrode is heated to a high temperature to generate thermal electrons. The filament 111e may be made of tungsten and may be heated by applying a voltage of 10 V and a current of about 3 to about 5 A to an electric wire 111f connected to the filament 111e.

In addition, when a high voltage of about 10 to about 300 kVp is applied between a negative electrode 111d and a positive electrode 111b, thermal electrons are accelerated and collide with a target material 111c of the positive electrode 111b, thereby generating X-rays. The generated X-rays are emitted outside via a window (111g), and a beryllium (Be) thin film may be used as the window 111g. In this regard, energy of the thermal electrons that collide with the target material 111c is mostly dissipated as heat and the remaining energy is converted into X-rays.

The positive electrode 111b is mainly made of copper, the target material 111c is disposed at a side of the positive electrode 111b that faces the negative electrode 111c, and the target material 111c may be a high-resistance material such as Cr, Fe, Co, Ni, W, Mo, or the like. The target material 111c illustrated in FIG. 6 may be rotated by a rotating field and, when the target material 111c is rotated, an electron impact area is increased and heat capacity per a unit area may be 10 times or more that when the target material 111c is in a fixed state.

A voltage applied between negative and positive electrodes of an X-ray tube is referred to as a tube voltage, and the magnitude of the voltage may be represented in peak kilovolts (kVp). When a tube voltage is increased, velocity of thermal electrons is increased and, consequently, the thermal electrons collide with a target material and thus energy of X-rays (energy of photons) is increased. Current flowing in the X-ray tube is referred to as tube current and may be represented as mean amperage (mA). When the tube current is increased, the number of thermal electrons released from a filament is increased and, consequently, the thermal electrons collide with the target material and thus a dose of the generated X-rays (the number of X-ray photons) is increased.

Accordingly, energy of X-rays may be controlled by a tube voltage, and the intensity or dose of X-rays may be controlled by tube current and X-ray exposure time.

The X-ray source 111 may emit monochromatic X-rays or polychromatic X-rays. When the X-ray source 111 emits polychromatic X-rays, energy band of X-rays may be defined by an upper limit and a lower limit.

The upper limit of the energy band, i.e., maximum energy of emitted X-rays, may be controlled by the magnitude of tube voltage, and the lower limit of the energy band, i.e., minimum energy of emitted X-rays, may be controlled by a filter inside or outside the X-ray generator 110. Average energy of emitted X-rays may be increased by filtering X-rays having a low energy band through a filter.

In addition, the X-ray imaging apparatus 100 may include an auto exposure controller (AEC) to control a parameter for X-ray emission, e.g., a parameter for at least one of a tube voltage, tube current, a target material of a positive electrode, exposure time, threshold energy, and a filter. The AEC serves to optimize X-ray emission conditions to suit an actual object to be X-ray imaged, and may set a parameter optimized to characteristics of the object by analyzing a pre-shot image of the object.

As illustrated in FIG. 7, the X-ray emission region is controlled while X-rays generated from the X-ray source 111 pass through the X-ray penetration region R of the collimator 113. X-rays directed towards a region outside the X-ray emission region set by the collimator control unit 131 are absorbed by the first, second, third and fourth blades 113a, 113b, 113c and 113d and shielded so that the X-rays are emitted to the set X-ray emission region, i.e., a region corresponding to the object region.

Although FIG. 7 illustrates a single collimator, a plurality of collimators may be configured in a vertical direction such that multiple X-ray emission regions can be controlled.

Figure 8A:
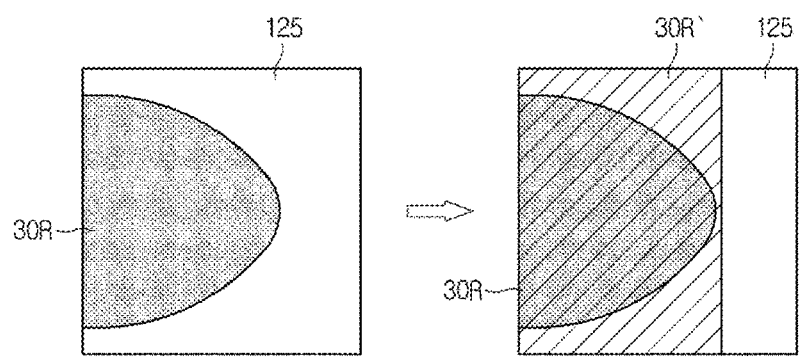
FIGS. 8A through 8C illustrate examples of X-ray emission regions.
Figure 8B:
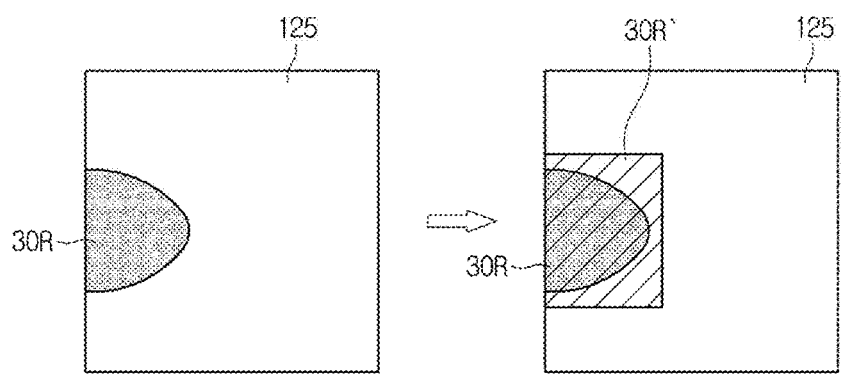
Figure 8C:
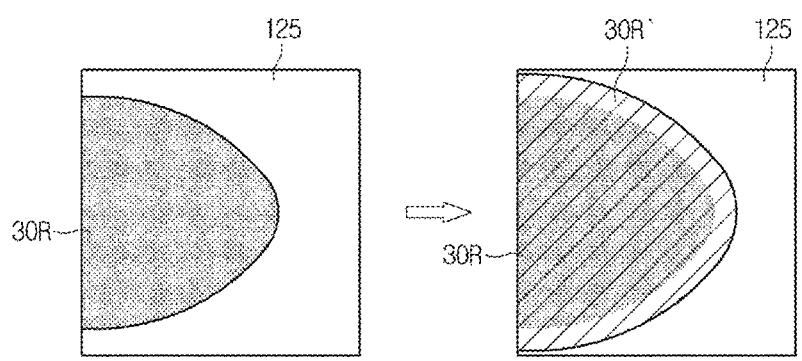

FIGS. 8A through 8C illustrate examples of X-ray emission regions. FIGS. 8A through 8C are top plan views of the touch sensor 125.

When the X-ray penetration region R of the collimator 113 has a tetragonal shape as illustrated in FIG. 5A, the X-ray emission region is also adjusted to have a tetragonal shape. When an object region 30R sensed by the touch sensor 125 is as illustrated in FIG. 8A, the first blade 113a illustrated in FIG. 5A may be moved in an −X-axis direction so that X-rays are emitted to an emission region 30R' illustrated in FIG. 8A.

In another embodiment, when the object region 30R sensed by the touch sensor 125 has a narrow width in a Y direction as illustrated in FIG. 8B, the first blade 113a illustrated in FIG. 5A may be moved in an −X-axis direction, the third blade 113c may be moved in a −Y-axis direction, and the fourth blade 113d may be moved in a Y-axis direction, so that X-rays are emitted to an emission region 30R' illustrated in FIG. 8B.

Meanwhile, when the collimator 113 forms a semi-oval X-ray penetration region R as illustrated in FIGS. 5B and 5C, the X-ray emission region 30R nearly coincides with the object region 30R as illustrated in FIG. 8C and thus emission of X-rays to an unnecessary region may be minimized and a radiation exposure dose may also be reduced.

Figure 9:
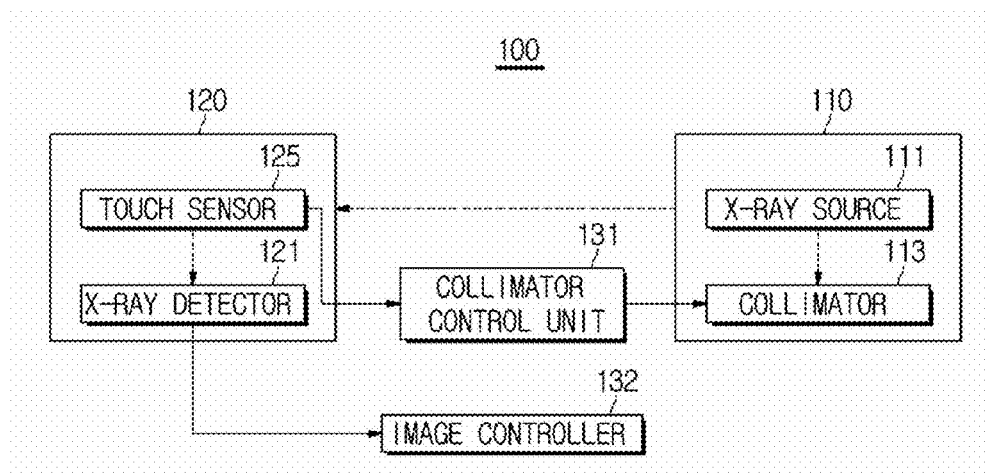
FIG. 9 is a control block diagram of the X-ray imaging apparatus capable of correcting error due to the touch sensor.

FIG. 9 is a control block diagram of the X-ray imaging apparatus 100 capable of correcting error due to the touch sensor 125.

As described above, X-ray data acquired by the X-ray detector 121 are used to generate an X-ray image of the object 30. For this operation, the X-ray imaging apparatus 100 may further include an image controller 132 to generate an X-ray image of the object 30 using the X-ray data. The image controller 132 removes error due to the touch sensor 125 from the transmitted X-ray data.

In particular, even though the touch sensor 125 is transparent, X-rays may be partially attenuated while passing through the touch sensor 125. Thus, the image controller 132 may remove attenuation effects by the touch sensor 125 from the X-ray data transmitted from the X-ray detector 121, whereby an X-ray image with better quality may be generated.

For example, the image controller 132 may pre-store a removal algorithm for the attenuation effects by the touch sensor 125 according to X-ray imaging conditions such as energy of X-rays, an exposure amount of X-rays, and the like, and may remove the attenuation effects by the touch sensor 125 by applying the pre-stored algorithm to the X-ray data acquired through emission of X-rays to the object 30.

In the above-described embodiment, the object region is determined using the touch sensor 125. In an X-ray imaging apparatus according to another embodiment of the present invention, however, an image of an object may be captured using a camera and an object region may be determined from the captured image.

Figure 10:
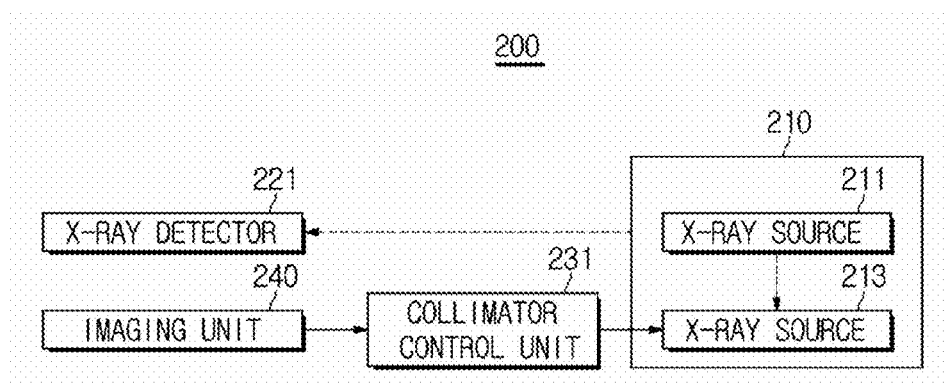
FIG. 10 is a control block diagram of an X-ray imaging apparatus according to another embodiment of the present invention.

FIG. 10 is a control block diagram illustrating an X-ray imaging apparatus 200 according to another embodiment of the present invention.

Referring to FIG. 10, the X-ray imaging apparatus 200 includes an X-ray generator 210 including an X-ray source 211 and a collimator 213, an imaging unit 240 to perform imaging of an object, an X-ray detector 221 to detect X-rays having passed through the object, and a collimator control unit 231 to determine an object region using an image captured by the imaging unit 240 and to control the collimator 213.

The X-ray generator 210 and the X-ray detector 221 have already been described above and thus detailed description thereof is omitted herein. In addition, the exterior view illustrated in FIG. 1 excluding the touch sensor 125 may also be applied to the present embodiment.

When an object, i.e., a breast, is compressed by the compression paddle 107, the imaging unit 240 performs imaging of the object. The imaging unit 240 needs to image location of the object on the X-ray detector 121, and thus, the imaging unit 240 may be installed above the X-ray detector 221. For example, the imaging unit 240 may be installed at a portion of the X-ray generator 210.

A captured image is transmitted to the collimator control unit 231, and the collimator control unit 231 determines an object region based on the captured image. That is, location of the object on the X-ray detector 221 is determined.

The collimator control unit 231 controls the collimator 213 such that an emission region of X-rays generated from the X-ray source 211 corresponds to an object region. A detailed description of control of the collimator 213 has already been provided above.

Hereinafter, an X-ray imaging apparatus control method according to an embodiment of the present invention will be described.

Figure 11:
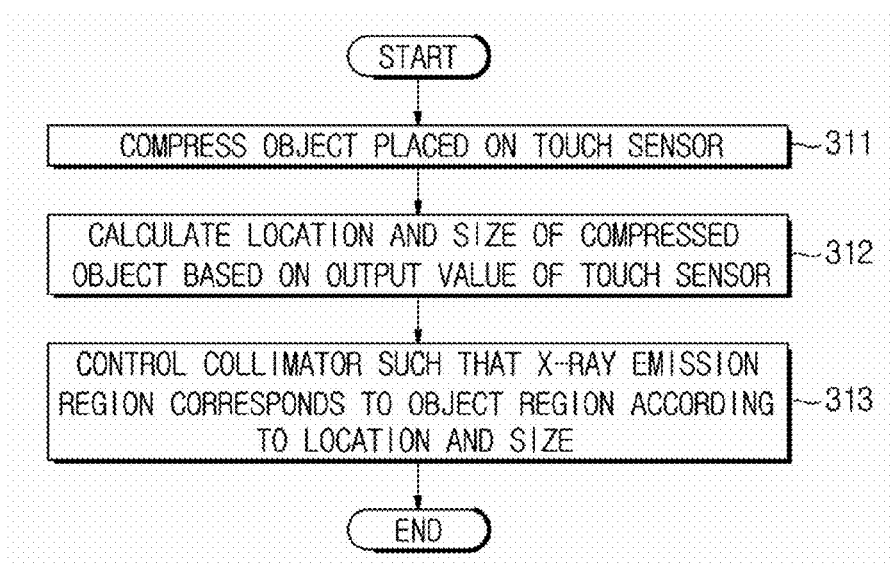
FIG. 11 is a flowchart illustrating an X-ray imaging apparatus control method according to an embodiment of the present invention.

FIG. 11 is a flowchart illustrating a method of controlling the X-ray imaging apparatus, according to an embodiment of the present invention.

Referring to FIG. 11, first, an object placed on the touch sensor 125 is compressed (operation 311). In this regard, the object is a breast and the touch sensor 125 may be a capacitive touch sensor or a resistive touch sensor. To obtain a high quality X-ray image, the object needs to be compressed as thin as possible, but the intensity of compression is determined by considering conditions of a patient and states of a breast.

Subsequently, location and size of the compressed object are calculated based on an output value of the touch sensor 125 (operation 312). A region in which the object is placed on the touch sensor 125, i.e., an object region, is determined according to the location and size of the object.

Then, the collimator 113 is controlled such that the emission region of X-rays corresponds to the object region according to the location and size of the object (operation 313). In particular, an X-ray emission region corresponding to the object region is set, and the collimator 113 is controlled such that X-rays are emitted to the set X-ray emission region.

As illustrated in FIG. 1, the collimator 113 is disposed in front of the X-ray source 111 and thus may adjust an emission region of X-rays emitted from the X-ray source 111. The collimator 113 includes at least one movable blade, and the blade may be made of a material having a high bandgap and thus absorb X-rays. X-rays pass through an empty space formed by the blade, and the empty space is referred to as an X-ray penetration region. That is, control of the collimator 113 indicates control of the X-ray penetration region through movement of the blade.

Figure 12:
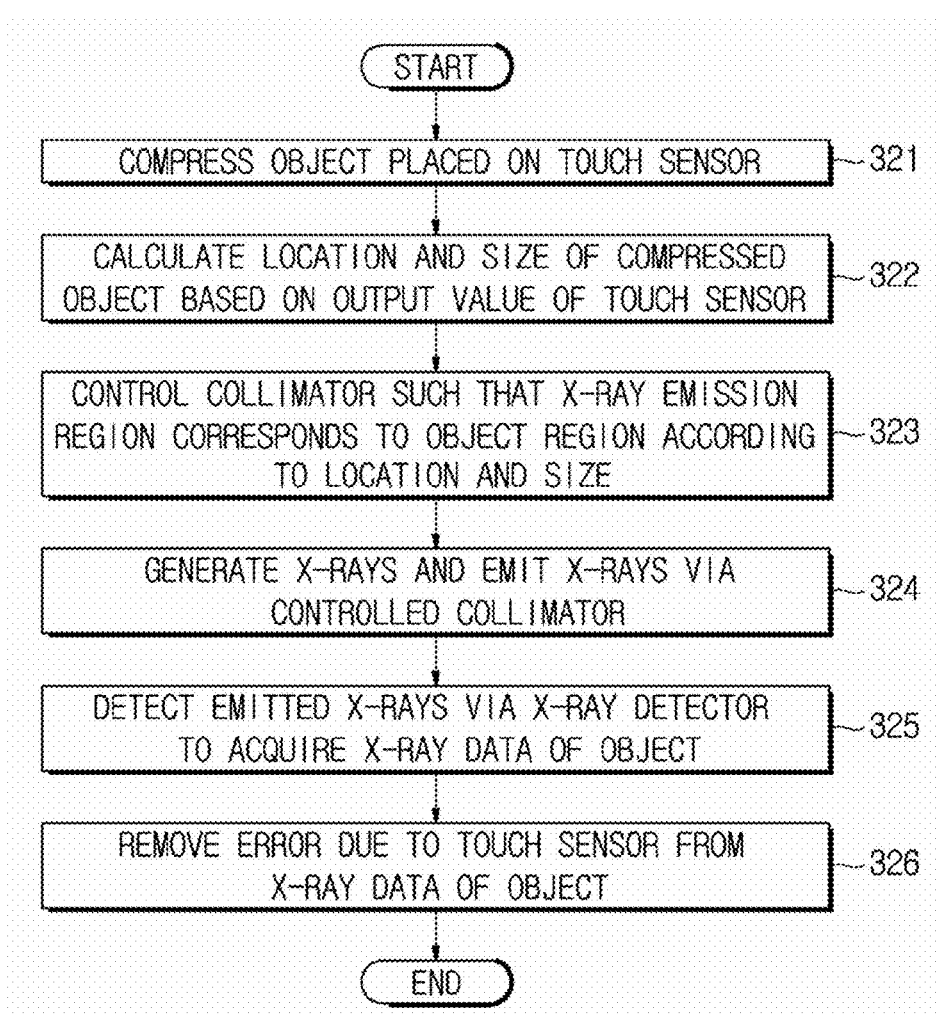
FIG. 12 is a flowchart illustrating an X-ray imaging apparatus control method that may remove error due to the touch sensor.

FIG. 12 is a flowchart illustrating an X-ray imaging apparatus control method that may remove error due to a touch sensor.

Referring to FIG. 12, first, an object placed on the touch sensor is compressed (operation 321). In this regard, the object is a breast and the touch sensor may be a capacitive touch sensor or a resistive touch sensor. To obtain a high quality X-ray image, the object needs to be compressed as thin as possible, but the intensity of compression is determined by considering conditions of a patient and states of a breast.

Subsequently, location and size of the compressed object are calculated based on an output value of the touch sensor (operation 322). A region in which the object is placed on the touch sensor, i.e., an object region, is determined according to the location and size of the object.

Then, a collimator is controlled such that the emission region of X-rays corresponds to the object region according to the location and size of the object (operation 323). In particular, an X-ray emission region corresponding to the object region is set, and the collimator is controlled such that X-rays are emitted to the set X-ray emission region.

When the collimator is controlled, X-rays are generated and are emitted via the collimator (operation 324). X-ray imaging conditions such as energy of the generated X-rays, an exposure amount of the X-rays, and the like may be automatically set by an AEC, or a radiologist may directly set X-ray imaging conditions by considering states of the object. When X-rays pass through the collimator, more particularly, the X-ray penetration region R of the collimator, the X-rays are finally emitted to the X-ray emission region set to correspond to the object region. The X-ray emission region may coincide with the object region according to a structure of the collimator. Although the X-ray emission region does not coincide with the object region, the X-ray emission region may minimally include a region outside the object region.

Then, X-ray data of the object are acquired by detecting the emitted X-rays using the X-ray detector (operation 325). X-rays having passed through the object and the touch sensor are detected and thus the acquired X-ray data include attenuation effects by both the object and the touch sensor, which act as error in an X-ray image.

Thus, error due to the touch sensor is removed from the X-ray data (operation 326). For example, a removal algorithm for the attenuation effects by the touch sensor according to X-ray imaging conditions such as energy of X-rays, an exposure amount of X-rays, and the like may be pre-stored, and the attenuation effects by the touch sensor 125 may be removed by applying the pre-stored algorithm to the X-ray data of the object.

According to the X-ray imaging apparatus and the control method therefor described in the above embodiments, a region of the compressed breast may be measured by the touch sensor and the collimator may be controlled such that the X-ray emission region corresponds to the measured region of the breast, whereby workflow for performing X-ray imaging may be reduced and subject pain due to breast compression may be alleviated.

In addition, unnecessary emission of X-rays is reduced and thus unnecessary radiation exposure dose may be decreased. Moreover, movement of a subject due to pain according to breast compression may be minimized, which helps improve X-ray image quality.

As is apparent from the above description, according to an X-ray imaging apparatus according to an embodiment of the present invention and a control method therefor, a region of a compressed breast is measured by a touch sensor and a collimator is controlled such that an X-ray emission region corresponds to the measured region of a compressed breast, whereby workflow for performing X-ray imaging may be reduced and subject pain due to breast compression may be alleviated.

In addition, unnecessary emission of X-rays is reduced and thus unnecessary radiation exposure dose may be decreased. Moreover, movement of a subject due to pain according to breast compression may be minimized, which helps improve X-ray image quality.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An X-ray imaging apparatus comprising:
   an X-ray source to generate X-rays and irradiate an object with the generated X-rays;
   a collimator to adjust an emission region of the X-rays generated from the X-ray source;
   an X-ray detector to detect X-rays having passed through the object to acquire X-ray data;
   a touch sensor disposed above the X-ray detector;
   a compression paddle to compress the object placed on the touch sensor; and
   a collimator control unit to calculate location and size of the compressed object based on an output value of the touch sensor and control the collimator based on calculation results.

2. The X-ray imaging apparatus according to claim 1, wherein the collimator control unit determines an object region according to the location and size of the compressed object and sets an X-ray emission region corresponding to the object region.

3. The X-ray imaging apparatus according to claim 2, wherein the collimator control unit controls the collimator such that the X-rays generated from the X-ray source are emitted to the set X-ray emission region.

4. The X-ray imaging apparatus according to claim 3, further comprising an image controller to remove error due to the touch sensor from the X-ray data.

5. The X-ray imaging apparatus according to claim 3, wherein the collimator comprises at least one blade movable in an X-axis direction and at least one driving unit to drive the at least one blade.

6. The X-ray imaging apparatus according to claim 5, wherein the at least one driving unit moves the at least one blade in an X-axis direction according to a control signal transmitted from the collimator control unit.

7. The X-ray imaging apparatus according to claim 6, wherein the collimator control unit calculates a displacement of the at least one blade, for correspondence between the X-ray emission region and the object region.

8. The X-ray imaging apparatus according to claim 7, wherein the collimator control unit transmits a control signal to the at least one driving unit so that the at least one blade is moved by the calculated displacement.

9. The X-ray imaging apparatus according to claim 8, wherein the collimator comprises a plurality of blades, the blades being each independently moved in an X-axis or Y-axis direction.

10. The X-ray imaging apparatus according to claim 3, wherein the touch sensor is at least one selected from the group consisting of a capacitive touch sensor and a resistive touch sensor.

11. A method of controlling an X-ray imaging apparatus comprising an X-ray source to generate X-rays and irradiate an object with the generated X-rays, a collimator to adjust an emission region of the X-rays generated from the X-ray source, and an X-ray detector to detect X-rays having passed through the object, the method comprising:
    compressing the object placed on a touch sensor installed above the X-ray detector;
    calculating location and size of the compressed object based on an output value of the touch sensor; and
    controlling the collimator based on calculation results.

12. The method according to claim 11, wherein the controlling comprises determining an object region according to the location and size of the compressed object and setting an X-ray emission region corresponding to the object region.

13. The method according to claim 12, wherein the controlling further comprises controlling the collimator such that the X-rays generated from the X-ray source are emitted to the set X-ray emission region.

14. The method according to claim 13, further comprising:
    generating X-rays from the X-ray source;
    emitting the X-rays via the controlled collimator;
    detecting the emitted X-rays through the X-ray detector to acquire X-ray data of the object; and removing error due to the touch sensor from the X-ray data of the object.

15. The method according to claim 13, wherein the collimator comprises at least one blade movable in an X-axis direction.

16. The method according to claim 15, wherein the controlling comprises moving the at least one blade in an X-axis direction.

17. The method according to claim 16, wherein the controlling further comprises calculating a displacement of the at least one blade, for correspondence between the X-ray emission region and the object region.

18. The method according to claim 17, wherein the controlling comprises moving the at least one blade by the calculated displacement.

19. The method according to claim 18, wherein the collimator comprises a plurality of blades, the controlling comprising each independently moving the blades in an X-axis direction.

20. The method according to claim 13, wherein the touch sensor is at least one selected from the group consisting of a capacitive touch sensor and a resistive touch sensor.

\* \* \* \* \*